United States Patent
Merklein

(10) Patent No.: US 6,317,205 B1
(45) Date of Patent: Nov. 13, 2001

(54) METHOD FOR MONITORING AN OPTICAL SYSTEM HAVING A FRONT LENS DISPOSED IMMEDIATELY AT A COMBUSTION CHAMBER, AND A DEVICE FOR CARRYING OUT THE METHOD

(75) Inventor: Thomas Merklein, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/835,346

(22) Filed: Apr. 16, 2001

Related U.S. Application Data

(63) Continuation of application No. PCT/DE99/03190, filed on Oct. 4, 1999.

(30) Foreign Application Priority Data

Oct. 16, 1998 (DE) .............................................. 198 47 832

(51) Int. Cl.$^7$ .................................................. G01N 21/00
(52) U.S. Cl. ........................................................ 356/239.2
(58) Field of Search ........................... 356/239.2, 239.8, 356/239.7, 237.2, 237.3, 213; 250/554; 364/148, 152, 550, 550.1

(56) References Cited

U.S. PATENT DOCUMENTS

| | | | |
|---|---|---|---|
| 3,744,873 | * 7/1973 | Jamison | 350/63 |
| 4,432,649 | * 2/1984 | Krause | 356/438 |
| 4,568,183 | * 2/1986 | Douglas | 356/43 |
| 5,487,266 | * 1/1996 | Brown | 60/39.06 |
| 5,812,270 | * 9/1998 | Hampton et al. | 356/394 |
| 5,914,489 | * 6/1999 | Baliga et al. | 250/339.05 |

FOREIGN PATENT DOCUMENTS

| | | |
|---|---|---|
| 1909029 | 1/1970 | (DE) . |
| 2847935 | 5/1980 | (DE) . |
| 2904126 | 8/1980 | (DE) . |
| 19710206A1 | 9/1998 | (DE) . |
| 0616200A1 | 9/1994 | (EP) . |

* cited by examiner

Primary Examiner—Frank G. Font
Assistant Examiner—Michael P. Stafira
(74) Attorney, Agent, or Firm—Herbert L. Lerner; Laurence A. Greenberg; Werner H. Stemer

(57) ABSTRACT

A method for monitoring an optical system having a front lens disposed immediately at a combustion chamber minimizes the time that the optical system is impaired for maintenance and cleaning work on the front lens. According to the invention, intensity values of the light of a flame of the combustion chamber are recorded for this purpose via the optical system, and the front lens surface is cleaned if necessary. In this process, a temperature value and a mean intensity value are determined from the intensity values, and then the relative degree of pollution of the front lens is determined therefrom and used for the purpose of determining a cleaning and/or maintenance time of the front lens.

4 Claims, 1 Drawing Sheet

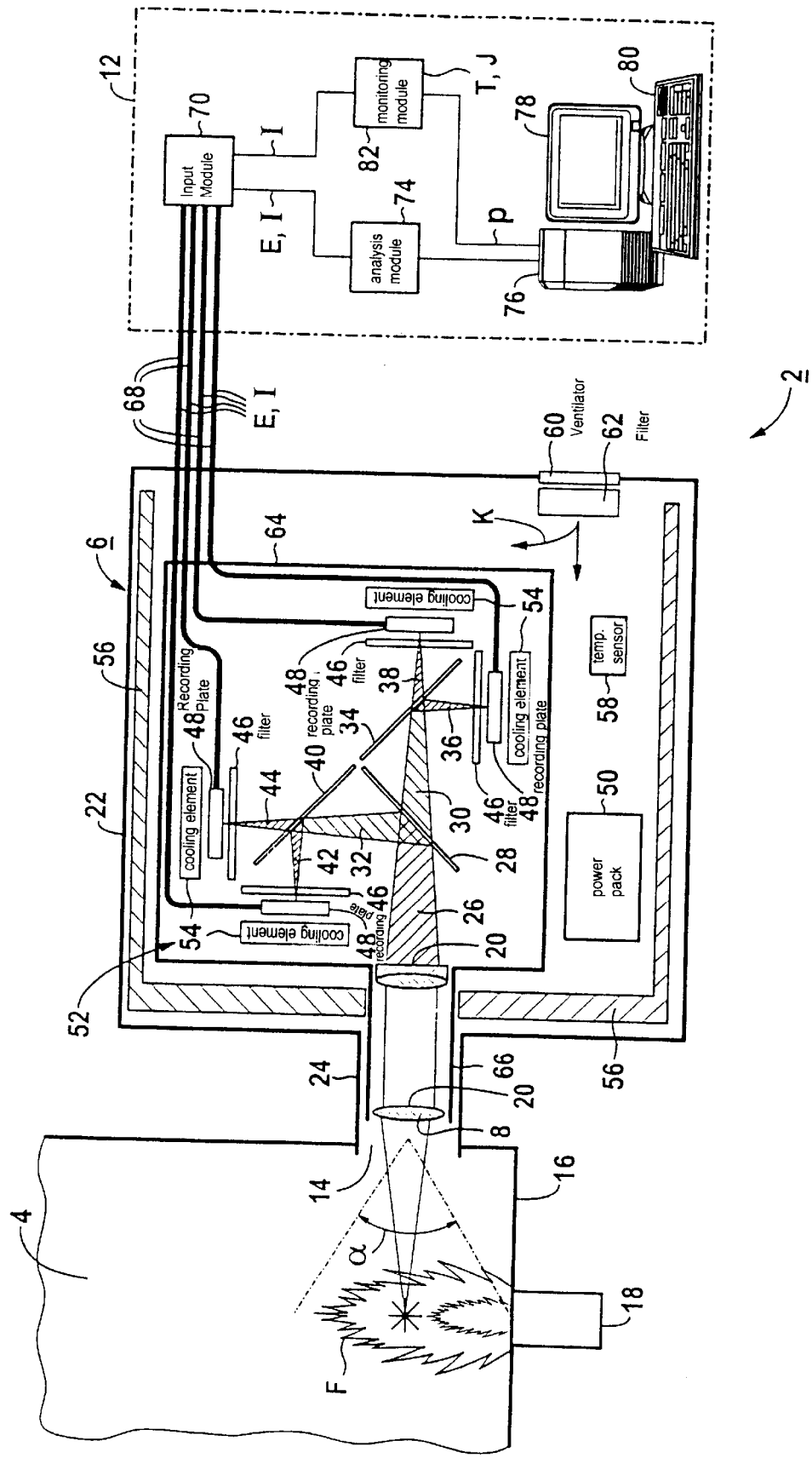

METHOD FOR MONITORING AN OPTICAL SYSTEM HAVING A FRONT LENS DISPOSED IMMEDIATELY AT A COMBUSTION CHAMBER, AND A DEVICE FOR CARRYING OUT THE METHOD

CROSS-REFERENCE TO RELATED APPLICATION

This application is a continuation of copending International Application No. PCT/DE99/03190, filed Oct. 4, 1999, which designated the United States.

BACKGROUND OF THE INVENTION

Field of the Invention

The invention relates to a method for monitoring an optical system having a front lens disposed immediately at a combustion chamber. It also relates to a device suitable for accomplishing the method.

In the combustion of fossil fuel or refuse in a combustion chamber, fluctuations in the calorific value of the fuel or of the fuel mixture occur because of the different origin of the fuel and/or because of the heterogeneous composition of the refuse. These fluctuations increase pollutant emission of the combustion process. These disadvantages also exist in the combustion of industrial residual material. In the case of which, the combustion of solid and liquid as well as gaseous fuels is usually provided simultaneously. Given knowledge of the parameters characterizing the combustion process, the firing control can be optimized, and thus the combustion process as well.

A device for combustion analysis can determine the parameters characterizing the combustion process. The device uses an optical system having a front lens disposed immediately at the combustion chamber, for example, to detect intensity values of the light of the combustion process that, in their totality, yield an image of a flame of the combustion process. The spatially resolved intensity values of the image can then be used, for example, to determine the temperature distribution and the concentration distribution of reaction products arising in the process of combustion. Such a device and a method suitable for operating the device are disclosed in German Published, Non-Prosecuted Patent Application DE 197 10 206 A1.

German Published, No n-Prosecuted Patent Application DE 28 47 935 A1 discloses a device for carrying out a method for finding pollutants on specimens in transmitted light, and for signaling changes in the transillumination of the specimen. Cleaning a transparent body as a function of the degree of pollution is disclosed in German Published, Non-Prosecuted Patent Application DE 29 04 126 A1.

A particular quality of the intensity values used for the analysis is important for reliable optical monitoring of the combustion process, and for a control based thereon. However, because waste products arise during combustion, pollution of the front lens of the optical system used to determine the intensity values, and thus a worsening of the quality of the data can arise. Consequently, there is a need at regular time intervals for time-consuming maintenance and/or cleaning of the front lens of the optical system, which is in direct contact with the combustion chamber. These time intervals are usually determined using empirical values and do not depend on the actual requirement for maintenance and/or cleaning of the front lens of the optical system. For safety reasons, maintenance and/or cleaning work is therefore usually provided more frequently than required for operating reasons. However, this is attended by long down times and a low level of availability of the optical system, and thus also of the combustion chamber.

SUMMARY OF THE INVENTION

It is accordingly an object of the invention to provide a method for monitoring an optical system having a front lens disposed immediately at a combustion chamber, and a device for carrying out the method that overcomes the hereinafore-mentioned disadvantages of the heretofore-known devices of this general type and that specifies a method for monitoring an optical system having a front lens disposed immediately at a combustion chamber, in the case of which a particularly low measure of down times, and thus a particularly high level of availability of the optical system is ensured without impairing the reliability of the optical system. This is to be achieved with a particularly low technical outlay in the case of a device suitable for carrying out the method.

With the foregoing and other objects in view, there is provided, in accordance with the invention, a method for monitoring an optical system. The method includes the first step of providing an optical system with a front lens disposed immediately at a combustion chamber. The next step is recording intensity values from a light of a flame of the combustion chamber with the optical system. The next step is determining a temperature value and a mean intensity value from the intensity values. The next step is determining a relative degree of pollution of the front lens from the temperature value and the mean intensity value. The next step is determining a maintenance time of the front lens.

In accordance with another mode of the invention, the method further includes cleaning the front lens after the maintenance time expires.

In accordance with another mode of the invention, the method further includes determining the mean temperature value of the flame from a first intensity value at a first wavelength and from a second intensity value at a second wavelength of the light of the flame of the combustion chamber.

With the objects of the invention in view, there is also provided a monitoring module for determining a cleaning time of an optical system having a front lens that is disposed immediately at a combustion chamber. The optical system measures a temperature value and a mean intensity value of a flame of the combustion chamber. The monitoring module includes a data processing system connected to the optical system calculating a relative degree of pollution of the front lens from the temperature value and the mean intensity value of the flame of the combustion chamber.

With reference to the method, the object is achieved according to the invention by using the optical system to record intensity values from the light of a flame of the combustion chamber. The front lens surface is cleaned if necessary. A temperature value and a mean intensity value are determined from the intensity values. The relative degree of pollution of the front lens is determined from the temperature value and the mean intensity value and used to determine a cleaning and/or maintenance time of the front lens.

In this case, the invention proceeds from the consideration that, for a particularly low measure of down times of the optical system, a fixed rhythm of maintenance and/or cleaning work for the front lens should not be prescribed. Rather, the front lens should be maintained and/or cleaned flexibly and as required with reference to the actual maintenance and/or cleaning requirement for it. Determining the time of carrying out the maintenance and/or cleaning work should be based in this case on measured data of the optical system. However, in this case impairing the operation of the optical system is to be avoided. If intensity values of the light of a flame of the combustion chamber are determined via the optical system during operation of the combustion chamber, it is possible to derive therefrom a measure of the relative degree of pollution of the front lens of the optical system. Specifically, pollution of the front lens causes a characteristic decrease in the intensity values. A particularly reliable determination of the relative degree of pollution of the front lens is given in this case by comparing an intensity value averaged from directly measured intensity values (actual intensity value) with an intensity value (desired intensity value) that has been determined from a temperature value determined for the flame.

The temperature value required for determining the degree of pollution of the front lens of the optical system is advantageously determined from an intensity value of a first wavelength and from an intensity value of a second wavelength of the light of the flame in the combustion chamber. For this purpose, two narrowband spectral regions each having a wavelength band of approximately ten nanometers (~10 nm) are coupled out of the radiation spectrum of the flame of the combustion chamber. In particular, these spectral regions are each situated in this case in a wavelength region without emission lines of the combustion product, in the so-called band-free regions. Specifically, according to Planck's radiation law, only Planck radiation is present in the band-free regions, and so it is possible to determine a temperature value of the light of the flame of the combustion chamber by forming the ratio of the intensity values of these spectral regions.

With reference to the device for determining the cleaning and/or maintenance time of an optical system having a front lens disposed immediately at the combustion chamber, the object is achieved by providing a monitoring module that determines with the aid of measured values of the optical system a temperature value and a mean intensity value of a flame of the combustion chamber, and determines therefrom the relative degree of pollution of the front lens.

The optical system can analyze the combustion of the combustion chamber, and for this purpose can record spatially resolved intensity values of individual flames of the combustion chamber. In this case, the intensity values can be used both for combustion analysis and for determining the degree of pollution of the front lens of the optical system. It is expedient in this case for the purpose of spatial resolution of the intensity values to provide a charge-coupled-device camera as recording plate. This CCD camera, also termed optical image sensor, in this case records the light emitted by the flame or the radiation spectrum of the flame.

In order to permit the use of the optical system directly at hot installation parts, for example at a boiler, it is expedient to provide a cooling system for the optical system. The cooling system in this case includes a Peltier element, for example. By using the Peltier effect, the Peltier element cools down with respect to the ambient temperature, whereas a heat sink connected to the Peltier element heats up. Moreover, the remaining electronic components, which belong to the optical system, can be cooled with the aid of cooling or purging air.

The advantages achieved with the invention include, in particular, in that determination of the relative degree of pollution of the front lens of the optical system permits maintenance and/or cleaning time to be determined with the aid of currently detected measured data. Consequently, maintenance and cleaning work on the front lens of the optical system need not be performed at a fixed time interval, but can be undertaken as required as a function of the determined relative degree of pollution of the front lens. Particularly short down times, and a particularly high level of availability of the optical system result therefrom.

Other features that are considered as characteristic for the invention are set forth in the appended claims.

Although the invention is illustrated and described herein as embodied in a method for monitoring an optical system having a front lens disposed immediately at a combustion chamber, and a device for carrying out the method, it is nevertheless not intended to be limited to the details shown, because various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWINGS

The sole FIGURE of the drawings is a partial block/partial schematic drawing of the optical system.

DESCRIPTION OF THE PREFERRED EMBODIMENTS

Referring now to the single FIGURE of the drawing, it is seen that a device 2 for combustion analysis serves the purpose of combustion analysis of the combustion process occurring in the combustion chamber 4. The device 2 for combustion analysis includes an optical system 6 with a front lens 8 disposed immediately at the combustion chamber 4, and a data processing system 12.

The firing or combustion chamber 4 is assigned to a steam-generating plant (not illustrated), for example a fossil-fired steam generator of a power plant or a garbage incineration plant. In order to monitor the combustion process proceeding in the combustion chamber 4, the optical system 6 detects via an opening 14 in the wall 16 of the combustion chamber 4 radiation data that are significant for the combustion and take the form of images, and feeds these to the data processing system 12. In this case, the optical system 6 is positioned on the wall 16 of the combustion chamber 4 with the aid of a fastener (not illustrated in more detail) in such a way as to produce as large a field of view as possible, that is to say a large viewing angle α, onto at least one flame F, produced in the combustion chamber 4 during combustion, of a burner 18 of the combustion chamber 4.

The optical system 6 includes a front lens 8, which is disposed immediately at the combustion chamber 4 and is assigned to an objective 20 that can include a plurality of lenses. The optical system 6 also includes a housing 22 with a cylindrical attachment 24. The radiation emanating from the flame F of the burner 18 penetrates the front lens 8 in a path of the image rays, such that beams 26 fall onto a beam splitter 28 connected downstream of the objective 20. In this case, the beams 26 also have the emission lines produced during the combustion, or band radiations of the reaction products of the combustion process.

The beam splitter 28 splits the beams 26 or the radiation spectrum of the flame F by physical beam splitting into a first and a second partial beam 30 and 32, respectively. The first partial beam 30 subsequently falls onto a further beam splitter 34. The further beam splitter 34 is disposed downstream of the beam splitter 28 with reference to the incident radiation. The beam splitter 34 splits the partial beam 30 into a first component 36 and into a second component 38. The second partial beam 32 likewise falls onto a further beam splitter 40, disposed downstream of the beam splitter 28 with reference to the beam path, and is split thereby into a first component 42 and a second component 44. The beam cross section remains unchanged in the respective splittings of the beams, that is to say the splitting of the beams 26 is performed uniformly over the entire cross section of the beam splitters 28, 34, 40 in accordance with their respective degrees of reflection and transmission. The beam splitters 28, 34, 40, which can, for example, be configured as line or narrowband filters, for example, therefore permit wavelength-dependent physical splitting of the beams 26 into a number of partial beams 30 and 32, respectively, and their respective components 36, 38 and 42, 44, which can, in turn, each have a prescribable spectral region. The spectral regions of the components 36, 38 and 42, 44, respectively, of the partial beams 30 and 32, respectively, can, if necessary, be further restricted by a number of correction filters 46, which are to be disposed directly downstream of the beam splitters 34 and 40, respectively. Further correction filters 46 can be provided as a function of the spectral regions, to be outcoupled, of the components 36, 38 and 42, 44, respectively, of the partial beams 30 and 32, respectively, of the beams 26 from the radiation spectrum of the flame F of the burner 18.

The spectral regions, filtered out of the radiation spectrum of the flame F, of the components 36, 38 and 42, 44, respectively, are imaged in each case onto an associated recording plate 48. The number of the recording plates 48 disposed in the optical system 8 is matched in this case to the number of the parameters required for monitoring the combustion process. It is, in particular, CCD image sensors with a spectral sensitivity of approximately three-hundred nanometers (~300 nm) to approximately one-thousand nanometers (~1,000 nm) that are used as recording plates 48, and so the entire visible radiation spectrum of the flame F can be detected without difficulty. The configuration and operating principle of such a CCD image sensor are known from the publication "Halbleiter-Optoelektronik" ["Semiconductor optoelectronics"] by Maximilian Bleicher, 1986, Dr. A. Hüthig Verlag, Heidelberg. In this case, the optical system 8 includes a power pack 50 for supplying power to the recording plates 48.

The optical system 6 includes a cooling system 52, in order to permit the optical system 6 to be used directly at the combustion chamber 4. In order to prevent noise in the image recorded by the recording plate 48, the operating temperature of each recording plate 48 must, specifically, be kept below an operating temperature of approximately 40° C. For each recording plate 48, the cooling system 52 in this case includes a cooling element 54, for example a Peltier element with a heat sink. The cooling system 52 also includes an insulation 56, in particular insulating wool, disposed on the inner wall of the housing 22. For the purpose of temperature measurement, the optical system 6 also includes a temperature sensor 58, for example a thermistor or a thermostatic switch, whose measured value is fed to a ventilator 60 in a way not illustrated in greater detail. A filter 62 for cleaning the cooling air K is connected upstream of the ventilator 60.

The recording plates 48 and the optical components, in particular the beam splitters 28, 34 and 40, the correction filter 46 and the objective 20 as well as the cooling elements 54 are surrounded by a chamber 64 or capsule disposed in the housing 22 in order to protect against pollutants. For example, the chamber 64 is configured in the form of a sheet-metal box with a cylindrical stub 66 disposed on a side face. The housing 22 is substantially matched to the shape of the chamber 64, the cylindrical attachment 24 of the housing 22 being inserted into the opening 14 in the wall 16 of the combustion chamber 4.

The recording plates 48 are connected in each case to the data processing system 12 via a line 68. The data processing system 12 includes an input module 70, an analysis module 74, a central module 76, as well as a display screen 78 and a data input device 80. The lines 68 open in each case into the input module 70. The input module 70 has a data connection to the analysis module 74. The analysis module 74, in turn, has a data connection to the central module 76. The central module 76 is connected to the display screen 78 and the data input device 80.

During operation of the combustion chamber 4, radiation data are detected via the optical system 6 for the purpose of monitoring the combustion process. The flame F of the burner 18 is detected in this case by the optical system 6. Depending on the positioning and viewing angle α of the optical system 6, the latter also can detect a plurality of flames F of a plurality of burners 18 at the same time. In other words, given a positioning of the optical system 6 at an angle of 90° to burners 18 disposed sequentially in a line, the optical system 6 can detect one or more flames F of the combustion chamber 4 in the case of a very large viewing window α.

For combustion analysis, the optical system 6 records emission lines E or band radiations of the reaction products of the combustion process and intensity values I of the light of the flame F of the burner 18. The temperature distribution and the concentration distribution of reaction products produced in the combustion process then can be determined from the spatially resolved emission lines E and the intensity values I of the image. A control (not illustrated in more detail) of the combustion process is based thereon.

The beams 26 of the flame F are radiated onto the beam splitter 28 via the front lens 8 and the optical system 6 in order to determine the emission lines E and intensity values I of the flame F of the combustion chamber 4. The beam splitter 28, in particular a yellow filter, transmits the first partial beam 30 with wavelengths of greater than 545 nm (yellowlight) and reflects the second partial beam 32 with wave-lengths of less than 500 nm (blue light). Subsequently, the beam splitter 34, in particular a red filter, is used to split the partial beam 30 impinging thereon into the first component 36 and the second component 38. In this case, the first reflected component 36 has wavelengths of less than 630 nm (orange light), and the second transmitted component 38 has wavelengths of more than 630 nm (red light). Because the first partial beam 30 includes only wavelengths of greater than 545 nm (yellow light), the first reflected component 36 has a bandwidth of 545 nm to 630 nm (orange light). The beam splitter 40 subdivides the second partial beam 32, reflected by the beam splitter 28, into the first component 42 with wavelengths of more than 400 nm (green light), and into the second component 44 with wavelengths of less than 400 nm. Because the second reflected partial beam 32 includes wavelengths of less than 500 nm (blue light), the transmitted first component 42 has a bandwidth of 400 nm to 500 nm (green light).

All light-deflecting or light-splitting optical components, for example color filters, prisms or mirrors, can be used as beam splitters 28, 34, and 40. The beam splitters 28, 34 and 40 used in the optical system 6 are so-called dichroic additive or subtractive color filters that both reflect the spectral region for a prescribable wavelength bandwidth, and transmit the spectral region of a second wavelength bandwidth. The splitting and filtering of the spectral regions can also be performed by aperture splitting and corresponding filtering.

The spectral regions of the components 36, 38 and 42, 44, respectively, filtered out by the beam splitters 28, 34 and 40, are limited to a bandwidth of approximately 10 nm by the correction filters 46. That is to say, the respective correction filters 46 limit the wavelengths of the components 36 and 38 to a bandwidth of 645 to 655 nm or 545 nm to 555 nm.

Similarly, the respective correction filters 46 limit the wavelengths of the components 42 and 44 to a bandwidth of 445 to 455 nm or of 375 to 385 nm. Interference filters with a bandwidth of 10 nm +/− 2 nm, in particular, are provided as correction filters 46.

The emission lines E and the intensity values I or the light of the components 36, 38 or 42, 44 filtered out in each case are recorded by the corresponding recording plates 48. The voltage values, resulting from the spatially resolved emission lines E and intensity values I of the images, of the recording plates 48 are then fed to the input module 70 of the data processing system 12. From there, these radiation data pass into the analysis module 74. There, the spatial distribution of the respective parameter, for example the temperature or the concentration of CO or of CN, is determined. The parameters relevant to the combustion analysis can then be represented on the display screen 78.

In order reliably to avoid errors due to pollution of the front lens 8 when detecting the radiation data used to analyze the combustion process, it is necessary to clean and/or maintain the front lens 8 of the optical system 6 at specific time intervals. The determination of the time for this cleaning and/or maintenance work is performed according to need by a monitoring module 82, which is assigned to the data processing system 12 and is connected in parallel with the analysis module 74.

For this purpose, the optical system 8 records intensity values I of the light of the flame F of the burner 18 of the combustion chamber 4. This is performed either separately and specifically for the determination of the relative degree of pollution of the front lens 8, or else within the framework of detecting measured data for the combustion analysis. To the extent they are detected in a separate measurement, these intensity values I are also fed to the input module 70 of the data processing system 12. The latter relays them using data processing technology to the monitoring module 82, in which the relative degree of pollution p of the front lens 8 is calculated.

The intensity values I are used for this purpose to determine a temperature value T of the flame F of the burner 18, from which a desired value is calculated in turn. This desired value is compared with a mean value of actually measured intensity values J, the actual value, and from this the relative degree of pollution p of the front lens 8 of the optical system 6 is yielded.

In order to determine the temperature value T of the flame F of the burner 18, use is made in this process in the exemplary embodiment of the intensity value I1 of the first component 36 of the first partial beam 30, and of the intensity value I2 of the second component 38 of the first partial beam 30. In this case, both the intensity value I1 and the intensity value I2 are each assigned a wavelength $\lambda 1$ and $\lambda 2$, respectively. The wavelength $\lambda 1$ or $\lambda 2$ associated with the intensity value I1 or I2, respectively, is in this case, for example, the passing wavelength of the correction filter 46, through which the first component 36 or the second component 38 of the first partial beam 30 passes. A temperature value T is determined for the flame F with the aid of the intensity value I1 of the wavelength $\lambda 1$ and the intensity value I2 of the wavelength $\lambda 2$, which relates to the same region of the image of the flame F. In this case, the two wavelengths $\lambda 1$ and $\lambda 2$ are selected in such a way that they are situated in a wavelength region without emission lines of a combustion product of the combustion chamber 4, in a so-called band-free region. For a point X of the flame F, the temperature value $T_x$ is yielded, in accordance with the ratio pyrometry at the point X, by using the formula:

$$T_X = \frac{C\left(\frac{1}{(\lambda 1)} - \frac{1}{(\lambda 2)}\right)}{\ln\left(\frac{I2_X}{I1_X} \cdot \frac{(\lambda 2)^5}{(\lambda 1)^5}\right)}$$

where $$C = \frac{hc}{k} = 1.438789 \cdot 10^{-2}\ mK,$$

h is Planck's constant,
c the speed of light in a vacuum, and
k is Boltzmann's constant.

$$I1_X = g_a(i_x^{(a)} - o_a),$$

$$I2_X = g_b(i_x^{(b)} - o_b),$$

where $i_x^{(a)}, i_x^{(b)}$ is the measured intensity value of the recording plate 48 at the point x, $o_a, o_b$ is an offset dependent on the respective recording plate 48, and $g_a, g_b$ is a gain factor dependent on the respective recording plate 48.

A mean intensity value J is now further determined from the measured intensity values I in order to determine the relative degree of pollution p of the front lens 8 of the optical system 6. Here, mean value signifies that the locally measured intensity values I are added up over a region of the image, and the resulting sum is divided by the number of the intensity values I. The result is then the mean intensity value J. Provided as intensity values I are, for example, those recorded by the recording plate 48 onto which the first component 36 of the first partial beam 30 has been directed. The mean intensity value J thus calculated is then related to the intensity value $I1_x$ that has been obtained from the above formula for the temperature value $T_x$ by solving the formula for $I1_x$ with the aid of the calculated temperature value $T_x$.

In accordance with single-wavelength pyrometry, the relative degree of pollution p of the front lens 8 of the optical system 6 can be determined from this with a conversion into percent as:

$$p = 100 \cdot \left(1 - \frac{g_a(J_a - o_a)}{\frac{K}{(\lambda I)^5} \exp\left(\frac{-K}{\lambda I \cdot T_x}\right)}\right) \text{ where}$$

$$K = \frac{2hc^2}{\Omega} = 3.7832 \cdot 10^{-16} Wm^2, \text{ and}$$

$\Omega$ is the solid angle that is determined by the calibration.

Using the determined relative degree of pollution p of the front lens 8 of the optical system 6, it is possible with the aid of empirical values to determine whether it is necessary to clean and/or maintain the optical system 6. There is thus no need to perform maintenance and cleaning work on the optical system 6 at a fixed time interval, but such work can be undertaken as a function of the determined relative degree of pollution p of the front lens 8 of the optical system 6. This results in particularly short down times of the optical system 6, and in a particularly high level of availability of the monitored combustion in the combustion chamber 4.

I claim:

1. A method for monitoring an optical system, which comprises:

providing an optical system with a front lens disposed immediately at a combustion chamber;

recording intensity values from a light of a flame in the combustion chamber with the optical system;

determining a temperature value and a mean intensity value from the intensity values;

determining a relative degree of pollution of the front lens from the temperature value and the mean intensity value; and determining a maintenance time of the front lens taking into account the temperature value and the mean intensity value.

2. The method according to claim 1, which further comprises cleaning the front lens after the maintenance time expires.

3. The method according to claim 1, which further comprises determining the mean temperature value of the flame from a first intensity value at a first wavelength and from a second intensity value at a second wavelength of the light of the flame of the combustion chamber.

4. A monitoring module for determining a cleaning time of an optical system having a front lens that is disposed immediately at a combustion chamber, the optical system measuring a temperature value and intensity valued of a flame in the combustion chamber, comprising a data processing system connected to the optical system for determining from the intensity values a mean intensity value and for calculating a relative degree of pollution of the front lens from the temperature value and the mean intensity value of the flame of the combustion chamber.

* * * * *